(12) United States Patent
Pape et al.

(10) Patent No.: US 8,122,905 B2
(45) Date of Patent: Feb. 28, 2012

(54) METHOD AND ARRANGEMENT FOR DIAGNOSIS OF A FINAL CONTROL ELEMENT

(75) Inventors: Detlef Pape, Nussbaumen (CH); Urs E. Meier, Würenlingen (CH); Andreas Stelter, Minden (DE)

(73) Assignee: ABB AG, Mannheim (DE)

( * ) Notice: Subject to any disclaimer, the term of this patent is extended or adjusted under 35 U.S.C. 154(b) by 767 days.

(21) Appl. No.: 11/984,518

(22) Filed: Nov. 19, 2007

(65) Prior Publication Data
US 2008/0121290 A1    May 29, 2008

(30) Foreign Application Priority Data

Nov. 25, 2006   (DE) .......................... 10 2006 055 747

(51) Int. Cl.
F16K 37/00   (2006.01)
F17D 3/01   (2006.01)
E21B 47/10   (2006.01)
G01F 1/20   (2006.01)

(52) U.S. Cl. .................... 137/554; 137/557; 73/152.32; 73/861.18

(58) Field of Classification Search .................. 137/553, 137/554, 557; 73/168, 152.32, 861.18
See application file for complete search history.

(56) References Cited

U.S. PATENT DOCUMENTS

| | | | | |
|---|---|---|---|---|
| 5,358,035 | A | * | 10/1994 | Grudzinski ..................... 166/53 |
| 5,524,484 | A | * | 6/1996 | Sullivan ............................. 73/168 |
| 5,558,115 | A | * | 9/1996 | Lenz et al. ........................ 137/86 |
| 6,530,277 | B2 | * | 3/2003 | Kumpfmueller ................. 73/592 |
| 6,840,233 | B2 | | 1/2005 | Lingenhult et al. | 
| 6,938,497 | B2 | * | 9/2005 | Arscott ....................... 73/861.23 |
| 2002/0062682 | A1 | | 5/2002 | Kumpfmueller | 
| 2003/0019297 | A1 | | 1/2003 | Fiebelkorn et al. |

FOREIGN PATENT DOCUMENTS

| | | |
|---|---|---|
| EP | 1 216 375 B1 | 6/2002 |
| EP | 1 477 678 A2 | 11/2004 |
| JP | 56-14672 A | 2/1981 |
| JP | 1-213539 A | 8/1989 |
| WO | WO 00/73688 A1 | 12/2000 |

OTHER PUBLICATIONS

Mundry, "Zustandsüberwachung an Prozessventilen mit intelligenten Stellungsreglern" Institut für fluidtechnische Antriebe und Steuerungen, Shaker Verlag Aachen 2002, 178 pages.

Willis et al., "Maintaining a Successful Valve and Trap Leak Detection Program using The ValveAlyzer® System" The 10th Annual Predictive Maintenance Technology National Conference, Training, and Exhibition Nov. 9-12, 1998, 37 Pages.

Office Action issued in the corresponding German Patent Application No. 10 2006 055 747.6-14 dated Apr. 16, 2009.

German Examination Report for DE 10 2006 055 747.6, dated Jun. 25, 2007.

* cited by examiner

*Primary Examiner* — John Rivell
*Assistant Examiner* — Atif Chaudry
(74) *Attorney, Agent, or Firm* — Buchanan Ingersoll & Rooney PC

(57) ABSTRACT

The disclosure relates to a method and an arrangement for diagnosis of a final control element, which is actuated by a pneumatically operated actuating mechanism under the control of a control device, and which emits acoustic signals during conventional use. It is proposed to detect acoustic signals fed back into the pneumatic system of the actuating mechanism, and to derive from them the status data of the final control element. For this purpose, an acoustic sensor is arranged in the pneumatic-fluid supply line of the actuating mechanism, with the acoustic sensor being electrically connected to an analysis device. A pressure sensor is used as the acoustic sensor.

4 Claims, 1 Drawing Sheet

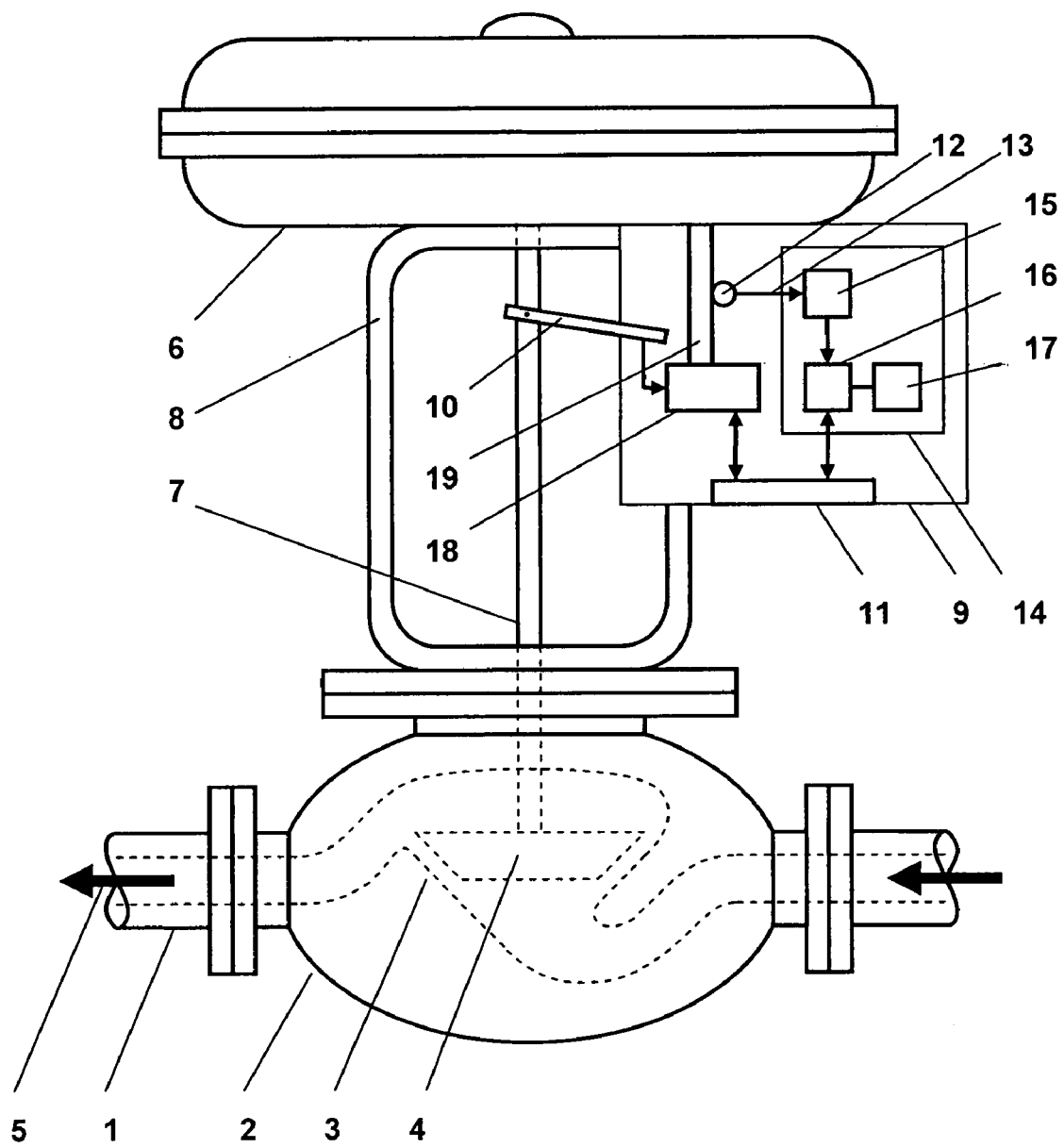

METHOD AND ARRANGEMENT FOR DIAGNOSIS OF A FINAL CONTROL ELEMENT

RELATED APPLICATIONS

This application claims priority under 35 U.S.C. §119 to German Patent Application No. 10 2006 055 747.6 filed in Germany on 25 Nov. 2006, the entire contents of which are hereby incorporated by reference in their entireties.

TECHNICAL FIELD

A method and an arrangement for diagnosis of a final control element are disclosed.

BACKGROUND INFORMATION

Control valves, as the type of final control elements in question, are generally known in automation and process engineering as extremely important elements in the control and regulation of processes. Their reliability is a crucial factor in the quality of the overall control process. Faults occurring during operation can result in failure of the entire system, with high maintenance costs as a consequence. Hence early diagnosis and thereby detection of faults in the valve can prevent such failures, and consequently also reduce the costs that arise from replacing, as a precaution, valves that are still working perfectly.

In particular, leaks from valves in the closed state are of significant diagnostic interest. The sealing action of the valve seating is reduced by ageing processes or dirt accumulation, and the process medium continues to flow through the valve despite a closed valve being signaled to the outer world.

Such leaks can be detected, for example, by a flow-rate sensor connected downstream that is installed additionally in the process line. Such a sensor is very expensive, however, and there is a high cost involved in fitting the sensor. In addition, the power consumption of the flow-rate sensor is normally so high that it cannot share the supply for the valve controller, but requires an additional supply line. Thus such a sensor is also normally only installed when it is already required for the process control system. In addition, it is known from the dissertation of Sebastian Maria Mundry "Zustandsüberwachung an Prozessventilen mit intelligenten Stellungsreglern" ["Monitoring the status of process valves using intelligent positioners"], Shaker Verlag, Aachen, 2002, that flow-rate sensors for measuring the maximum flow rate are not suitable for reliable detection of the low flow rates from leaks.

It is also known from the same publication that the flow of a fluid under pressure through a narrow aperture produces an acoustic signal as a result of various physical effects. For instance, the high flow rates that arise cause severe turbulence after the aperture, and the pressure drop in the flow results in cavitation. The turbulence and the collapse of the cavitation bubbles produce an acoustic signal that is directly dependent on the flow rate and the fluid properties. At low rates, the signal is composed of individual acoustic pulses generated by the collapse of the individual cavitation bubbles, and develops into white noise at high rates. This acoustic signal is overlaid by the general process sounds in the plant, which are produced by pumps, general flow noises, chemical processes etc.

As these process sounds propagate in the pipeline system of the plant, the sounds are attenuated by different amounts depending on their frequency. The high frequencies, in particular, are strongly attenuated, so that generally process sounds are only detectable at the valve as low-frequency acoustic signals (in the kHz range). Thus the sounds produced by the leak can be discriminated from the general process sounds by measuring in higher frequency ranges. It is known from Leak Detection Service, Maintaining a Successful Valve and Trap Leak Detection Program using the Valve-Analyser System, The 10th Annual Predictive Maintenance Technology National Conference, Nov. 9-12, 1998, that valve service companies currently use ultrasound sensors in order to measure the acoustic signals directly at the valve, i.e. close to the noise source. In addition, these signals are also compared with the signals from ultrasound sensors installed further upstream and downstream in the pipeline system. A leak can then be detected from these signals, and, with suitable calibration, it is even possible to determine the size of the leak for the valve from the signal level.

Furthermore, EP 1216375 B1 and WO 00/73688 A1 disclose detecting the structure-borne noise on the valve casing or on parts directly connected to this, and supplying this information to the positioner, in which it is evaluated and processed. The valve is continuously monitored, with the electronics and position signal already available in the positioner being shared for the diagnosis. The publications also disclose that high-frequency signals (>50 kHz) are analyzed, and that the ultrasound spectrum in the closed state is compared with a signal in the slightly open state. The latter method can be applied equally well to reducing the ambient noise without comparative measurements needing to be made at different points in the direction of flow and against the direction of flow. Although sharing the use of the position-sensor electronics and the position signal does reduce the installation costs for this diagnostic system, the ultrasound sensor head itself must still be fitted on the valve as an additional external unit.

SUMMARY

An exemplary method is disclosed for diagnosis of a final control element, which is actuated by a pneumatically operated actuating mechanism under the control of a control device, and which emits acoustic signals during conventional use. Acoustic signals fed back into the pneumatic system of the actuating mechanism are detected, from which the status data of the final control element is derived.

An exemplary arrangement is disclosed for diagnosis of a final control element, which is actuated by a pneumatically operated actuating mechanism under the control of a control device, and which emits acoustic signals during conventional use. An acoustic sensor is arranged in the pneumatic-fluid supply line of the actuating mechanism, with the acoustic sensor being electrically connected to an analysis device.

An exemplary method is disclosed for diagnosis of a final control element, which is actuated by a pneumatically operated actuating mechanism under the control of a control device, and which emits acoustic signals during conventional use. A pressure sensor is used as the acoustic sensor.

BRIEF DESCRIPTION OF THE DRAWING

The disclosure is explained in greater detail below with reference to an exemplary embodiment.

The single FIGURE shows a process valve 2 in relation to an exemplary section of a pipeline 1.

DETAILED DESCRIPTION

Hence an object of the disclosure is to detect acoustic signals emanating from the final control element to be monitored, at minimum possible expense and under continued use of the existing means necessary for the conventional use of the final control element.

The disclosure is based on a final control element, which is actuated by a pneumatically operated actuating mechanism under the control of a control device, and which emits acoustic signals during conventional use. The acoustic signals propagate in the final control element and are fed back into the pneumatic system of the actuating mechanism via the elements directly connected to the final control element. In this case, the acoustic signals are mainly transferred via the rod onto the membrane in the actuating mechanism and into the housing of the actuating mechanism, which amplify these signals like a large loudspeaker membrane and transfer them to the pneumatic fluid. Inside the actuating mechanism, in particular, strong amplification of the acoustic signal takes place in the pneumatic fluid of the drive chamber.

According to the disclosure, the acoustic signals fed back into the pneumatic system of the actuating mechanism are detected, and the status data of the final control element is derived from these signals. According to a feature of the invention relating to the apparatus, it is provided for this purpose that an acoustic sensor is arranged in the pneumatic-fluid supply line of the actuating mechanism, with the acoustic sensor being electrically connected to an analysis device.

The fed-back acoustic signals can be picked up at any point in the pneumatic system, so that an easily accessible location for the signal detector can be selected, even if the actuating mechanism itself is rather inaccessible.

The amplified acoustic signal is additionally transferred to the control device via the pneumatic-fluid supply lines, without the need for any direct physical contact between the control device and the valve system. The pneumatic-fluid pipelines can also screen the acoustic signal even from ambient noise.

In an exemplary embodiment of the disclosure, the fed-back acoustic signals are detected in the control device. In this case, detection of the acoustic signal and processing of the acoustic signal can take place in the same physical location.

According to a further feature of the disclosure, it can be provided that the status data of the final control element is derived from the amplitude spectrum of the fed-back acoustic signals. In this case, the occurrence of characteristic spectral images being used to infer associated status conditions of the final control element.

According to an alternative feature of the disclosure, it can be provided that the status data of the final control element is derived from the levels of the fed-back acoustic signals. This feature is based on the knowledge that the status of the final control element can already be inferred just from the intensity of the fed back acoustic signal.

According to another alternative feature of the disclosure, it can be provided that the status data of the final control element is derived from characteristic patterns of the fed-back acoustic signals. This is based on the knowledge that certain status conditions of the final control element can be assigned a respective characteristic acoustic pattern, which when recognized in the fed back acoustic signal indicates the respective status.

According to another feature of the disclosure, it can be provided that the detected acoustic signals are transferred electronically to a central device for analysis and evaluation. In this case, the means and resources required, e.g., for the complex pattern recognition can be kept centrally at a location for a plurality of detectors.

According to an alternative feature of the disclosure, it can be provided that the detected acoustic signals are analyzed and evaluated in the control device. The means for detecting and for processing the detected acoustic signals are located immediately beside each other. This avoids any errors arising in the signal.

Finally, according to another feature of the disclosure, it can be provided that a pressure sensor is used as the acoustic sensor. Such pressure sensors can be present in the control device for monitoring the control pressure for the actuating mechanism, so that no additional means are required.

The disclosure is explained in greater detail below with reference to an exemplary embodiment. The single FIGURE shows a process valve 2 installed in a section of a pipeline 1, which is part of a process plant (not shown further), installed in a process valve 2. Inside the process valve 2 there is a closing body 4 that interacts with a valve seating 3 in order to control the quantity of process medium 5 passing through. The closing body 4 is operated linearly by an actuating mechanism 6 via a rod 7. The actuating mechanism 6 is connected to the process valve 2 via a yoke 8. A positioner 9 is mounted on the yoke 8. The travel of the rod 7 into the positioner 9 is signaled via a position sensor 10. The detected travel is compared in a control unit 18 with the setpoint value supplied via a communications interface 11, and the actuating mechanism 6 is controlled as a function of the detected control deviation. The control unit 18 of the positioner 9 comprises an I/P converter for converting an electrical control deviation into an appropriate control pressure. The I/P converter of the control unit 18 is connected to the actuating mechanism 6 via a pneumatic-fluid supply line 19.

An acoustic sensor 12 is arranged in the pneumatic-fluid supply line 19 of the actuating mechanism 6. The acoustic measurement signal 13 from the sensor 12 is received by a signal acquisition device 15, and evaluated in a signal processing device 16 connected to its output. A memory device 17 is assigned to the signal processing device 16. In addition, the signal processing device 16 is connected to the communications interface 11 in order to signal the diagnostic result to a higher-level device (not shown).

During conventional use, vibrations are excited in the process valve 2 as a function of its operating status. The excitations can have various causes as mentioned in the introduction, and result in acoustic signals appearing in different frequency ranges. For instance, acoustic signals in the region of several kilohertz indicate a leak, whereas low-frequency acoustic signals point to vibrations of the process valve 2.

These acoustic signals propagate in the process valve 2 and are fed back into the pneumatic system 19 of the actuating mechanism 6 via the elements directly connected to the process valve 2. In this case, the acoustic signals are mainly transferred via the valve rod 7 onto the membrane in the actuating mechanism 6 and into the housing of the actuating mechanism 6, which amplify these signals like a large loudspeaker membrane and transfer them to the pneumatic fluid. Inside the actuating mechanism 6, in particular, strong amplification of the acoustic signal takes place in the pneumatic fluid of the drive chamber.

The acoustic signals also propagate into the pneumatic-fluid supply line 19 between the I/P converter of the control unit 18 and the actuating mechanism 6. The acoustic signals are detected here by the acoustic sensor 12. Using a pressure sensor as the acoustic sensor 12 is particularly advantageous in this case. Such a pressure sensor is part of the I/P converter of the control unit 18, and is used for regulating the control pressure for the actuating mechanism 6. Additional acoustic sensors 12 can hence be dispensed with. Thus leak detection can be implemented as a pure software solution in the positioner 9.

In addition to leak detection, it is also possible to use the procedure described above for acoustic measurement of the acoustic signals to evaluate and analyze sounds other than the flow sounds used above. These include particularly, but not exclusively, vibrations of the valve or other fault sources, which a technician would currently identify on-site by listening. It can be provided in this case to process these additional sounds by suitable acoustic analysis in the device or by transferring the sounds to a central device where they can be analyzed by a technician, without the technician needing to go to the site of the valve. Whenever a strong, unusual sound arises, for example at the valve, this can be transferred to the central device in the form of an acoustic file for diagnosis. Both manual and automated analysis of the received acoustic file can be provided in the central device.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

| List of references | |
|---|---|
| 1 | pipeline |
| 2 | process valve |
| 3 | valve seating |
| 4 | closing body |
| 5 | process medium |
| 6 | actuating mechanism |
| 7 | valve rod |
| 8 | yoke |
| 9 | positioner |
| 10 | position sensor |
| 11 | communications interface |
| 12 | acoustic sensor |
| 13 | acoustic measurement signal |

| List of references -continued | |
|---|---|
| 14 | diagnostic unit |
| 15 | signal acquisition device |
| 16 | signal processing device |
| 17 | memory device |
| 18 | control unit |
| 19 | pneumatic-fluid supply line |

What is claimed is:

1. An arrangement for diagnosis of a final control element, which is actuated by a pneumatically operated actuating mechanism under the control of a control device, and which emits acoustic signals during conventional use, wherein the actuating mechanism comprises a pneumatic-fluid supply line supplying pneumatic fluid for pneumatic operation of the actuating mechanism, and wherein the arrangement comprises:
   an acoustic sensor arranged in the pneumatic-fluid supply line of the actuating mechanism, the acoustic sensor being configured to detect acoustic signals fed back into the pneumatic-fluid supply line from the final control element; and
   an analysis device electrically connected to the acoustic sensor, the analysis device being configured to derive the status data of the final control element based on the detected acoustic signals.

2. The arrangement as claimed in claim 1, wherein the analysis device is formed by the control device of the actuating mechanism.

3. The arrangement as claimed in claim 1, wherein the analysis device is formed by a remote central device.

4. The arrangement as claimed in claim 1, comprising:
   a rod connected between the actuating mechanism and the final control element,
   wherein the sensor detects the acoustic signals which propagate from the final control element and through the rod into the pneumatic-fluid supply line.

\* \* \* \* \*